(12) United States Patent
Agrawal et al.

(10) Patent No.: US 10,737,086 B2
(45) Date of Patent: Aug. 11, 2020

(54) HEMOSTASIS VALVES AND METHODS FOR MAKING AND USING HEMOSTASIS VALVES

(71) Applicant: BOSTON SCIENTIFIC LIMITED, Hamilton (BM)

(72) Inventors: Sumit Agrawal, Haryana (IN); Mayank Bhatnagar, Delhi (IN); Peeyush Tomar, Uttar Pradesh (IN); Poornachandra Nayak, Karnataka (IN); Anshul Chabra, Delhi (IN)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 176 days.

(21) Appl. No.: 15/907,875

(22) Filed: Feb. 28, 2018

(65) Prior Publication Data
US 2018/0256874 A1 Sep. 13, 2018

Related U.S. Application Data

(60) Provisional application No. 62/470,617, filed on Mar. 13, 2017.

(51) Int. Cl.
*A61M 39/06* (2006.01)
(52) U.S. Cl.
CPC ........ *A61M 39/0613* (2013.01); *A61M 39/06* (2013.01); *A61M 39/0693* (2013.01);
(Continued)
(58) Field of Classification Search
CPC .......... A61M 2207/00; A61M 39/0613; A61M 2039/062; A61M 2039/0633;
(Continued)

(56) References Cited

U.S. PATENT DOCUMENTS 2,833,568 A 5/1958 Corsette
3,095,175 A 6/1963 Taisho
(Continued)

FOREIGN PATENT DOCUMENTS

WO 9945983 A1 9/1999

OTHER PUBLICATIONS

PCT Search Report and Written Opinion for PCT/US2009/039396 dated Apr. 3, 2009.
(Continued)

*Primary Examiner* — Brandy S Lee
(74) *Attorney, Agent, or Firm* — Seager, Tufte & Wickhem LLP

(57) ABSTRACT

Hemostasis valves and methods for making and using hemostasis valves are disclosed. An example hemostasis valve may include a main body having a distal end region and a proximal end region. A first seal member may be disposed within the proximal end region of the main body. A cartridge may be at least partially disposed within the proximal end region of the main body. The cartridge may include a second seal member. A plunger may be coupled to the proximal end region of the main body. A rotation limiting member may be positioned adjacent to the proximal end region of the main body. A tab member may be positioned adjacent to the proximal end region of the main body. The tab member may be designed to rotate relative to the proximal end region of the main body until the tab member engages the rotation limiting member.

20 Claims, 12 Drawing Sheets

(52) U.S. Cl.
CPC .......... *A61M 2039/064* (2013.01); *A61M 2039/0633* (2013.01); *A61M 2039/0686* (2013.01); *A61M 2207/00* (2013.01)

(58) Field of Classification Search
CPC .... A61M 2039/064; A61M 2039/0686; A61M 39/06; A61M 39/0693
See application file for complete search history.

(56) References Cited

U.S. PATENT DOCUMENTS

| | | |
|---|---|---|
| 3,685,786 A | 8/1972 | Woodson |
| 4,612,010 A | 9/1986 | Hamacher et al. |
| 4,723,550 A | 2/1988 | Bales et al. |
| 4,857,062 A | 8/1989 | Russell |
| 4,875,062 A | 10/1989 | Rakov |
| 4,895,346 A | 1/1990 | Steigerwald |
| 4,925,450 A | 5/1990 | Imonti et al. |
| 4,932,114 A | 6/1990 | Morse et al. |
| 4,932,633 A | 6/1990 | Johnson et al. |
| 4,978,341 A | 12/1990 | Niederhauser |
| 5,009,391 A | 4/1991 | Steigerwald |
| 5,030,206 A | 7/1991 | Lander |
| 5,049,071 A | 9/1991 | Davis et al. |
| 5,059,186 A | 10/1991 | Yamamoto et al. |
| 5,060,987 A | 10/1991 | Miller |
| 5,078,433 A | 1/1992 | Morse et al. |
| 5,078,688 A | 1/1992 | Lobodzinksi et al. |
| 5,098,393 A | 3/1992 | Amplatz et al. |
| 5,106,054 A | 4/1992 | Mollenauer et al. |
| 5,135,492 A | 8/1992 | Melker et al. |
| 5,158,553 A | 10/1992 | Berry et al. |
| 5,161,773 A | 11/1992 | Tower |
| 5,167,636 A | 12/1992 | Clement |
| 5,195,980 A | 3/1993 | Catlin |
| 5,197,463 A | 3/1993 | Jeshuran |
| 5,203,774 A | 4/1993 | Gilson et al. |
| 5,205,831 A | 4/1993 | Ryan et al. |
| 5,224,929 A | 7/1993 | Remiszewski |
| 5,241,990 A | 9/1993 | Cook |
| 5,269,764 A | 12/1993 | Vetter et al. |
| 5,269,771 A | 12/1993 | Thomas et al. |
| 5,273,546 A | 12/1993 | Mclaughlin et al. |
| 5,282,790 A | 2/1994 | Clement |
| 5,299,843 A | 4/1994 | Weigl et al. |
| 5,324,271 A | 6/1994 | Abiuso et al. |
| 5,338,313 A | 8/1994 | Mollenauer et al. |
| 5,350,205 A | 9/1994 | Aldridge et al. |
| 5,350,364 A | 9/1994 | Stephens et al. |
| 5,352,215 A | 10/1994 | Thome et al. |
| 5,356,394 A | 10/1994 | Farley et al. |
| 5,364,371 A | 11/1994 | Kamen |
| 5,376,077 A | 12/1994 | Gomringer |
| 5,382,230 A | 1/1995 | Bonn |
| 5,383,860 A | 1/1995 | Lau |
| 5,389,090 A | 2/1995 | Fischell et al. |
| 5,395,349 A | 3/1995 | Quiachon et al. |
| 5,460,615 A | 10/1995 | Storz |
| 5,514,109 A | 5/1996 | Mollenauer et al. |
| 5,542,933 A | 8/1996 | Marks |
| 5,562,611 A | 10/1996 | Transue |
| 5,569,208 A | 10/1996 | Woelpper et al. |
| 5,575,767 A | 11/1996 | Stevens |
| 5,584,314 A | 12/1996 | Bron |
| 5,591,137 A | 1/1997 | Stevens |
| 5,599,327 A | 2/1997 | Sugahara et al. |
| 5,651,170 A | 7/1997 | Stevens |
| 5,693,025 A | 12/1997 | Stevens |
| 5,911,710 A | 6/1999 | Barry et al. |
| 5,921,968 A | 7/1999 | Lampropoulos et al. |
| 5,935,112 A | 8/1999 | Stevens et al. |
| 5,935,122 A | 8/1999 | Fourkas et al. |
| 5,992,899 A | 11/1999 | Strowe |
| 6,287,280 B1 | 9/2001 | Lampropoulos et al. |
| 6,331,176 B1 | 12/2001 | Becker et al. |
| 6,402,723 B1 | 6/2002 | Lampropoulos et al. |
| 6,458,103 B1 | 10/2002 | Albert et al. |
| 6,572,590 B1 | 6/2003 | Stevens et al. |
| 6,695,818 B2 | 2/2004 | Wollschlger |
| 6,986,749 B2 | 1/2006 | Wollschlger |
| 7,172,580 B2 | 2/2007 | Hruska et al. |
| 7,938,809 B2 | 5/2011 | Lampropoulos et al. |
| 8,777,893 B2 | 7/2014 | Malewicz |
| 9,592,372 B2 | 3/2017 | Myers |
| 2001/0021825 A1 | 9/2001 | Becker et al. |
| 2004/0172008 A1 | 9/2004 | Layer |
| 2005/0171479 A1 | 8/2005 | Hruska et al. |
| 2007/0106262 A1 | 5/2007 | Becker et al. |
| 2008/0157017 A1* | 7/2008 | Macatangay ..... A61M 39/0613 251/314 |
| 2008/0208175 A1 | 8/2008 | Beckman et al. |
| 2009/0259200 A1 | 10/2009 | Lampropoulos et al. |
| 2013/0006176 A1 | 1/2013 | Miller |
| 2014/0207083 A1 | 7/2014 | Pessin |
| 2018/0126143 A1 | 5/2018 | Agrawal et al. |

OTHER PUBLICATIONS

International Search Report and Written Opinion for Application No. PCT/US2018/020202, 14 pages, dated May 25, 2018.

* cited by examiner

HEMOSTASIS VALVES AND METHODS FOR MAKING AND USING HEMOSTASIS VALVES

CROSS REFERENCE TO RELATED APPLICATIONS

This application claims the benefit of U.S. Provisional Patent Application Ser. No. 62/470,617 filed on Mar. 13, 2017, the disclosure of which is incorporated herein by reference.

TECHNICAL FIELD

The present disclosure pertains to medical devices, and methods for manufacturing medical devices. More particularly, the present disclosure pertains to hemostasis valves and methods for making and using hemostasis valves.

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example hemostasis valve is disclosed. The hemostasis valve comprises: a main body having a distal end region and a proximal end region; a first seal member disposed within the proximal end region of the main body; a cartridge at least partially disposed within the proximal end region of the main body, the cartridge including a second seal member; a plunger coupled to the proximal end region of the main body; a rotation limiting member positioned adjacent to the proximal end region of the main body; and a tab member positioned adjacent to the proximal end region of the main body, the tab member being designed to rotate relative to the proximal end region of the main body until the tab member engages the rotation limiting member.

Alternatively or additionally to any of the embodiments above, the rotation limiting member is disposed along an outer surface of the main body.

Alternatively or additionally to any of the embodiments above, the tab member is disposed along the plunger.

Alternatively or additionally to any of the embodiments above, the rotation limiting member is disposed along an inner surface of the plunger.

Alternatively or additionally to any of the embodiments above, the tab member is disposed along the proximal end region of the main body.

Alternatively or additionally to any of the embodiments above, the proximal end region of the main body includes one or more threads.

Alternatively or additionally to any of the embodiments above, further comprising a nut threadably engaged with the one or more threads.

Alternatively or additionally to any of the embodiments above, the rotation limiting member comprises a stopping face formed on the cartridge, wherein the tab member comprises a guiding protrusion formed along the nut.

Alternatively or additionally to any of the embodiments above, an axial slot is formed in the one or more threads.

Alternatively or additionally to any of the embodiments above, the tab member is designed to axially slide along the axial slot in the one or more threads.

Alternatively or additionally to any of the embodiments above, a ring member is disposed about the proximal end region of the main body.

Alternatively or additionally to any of the embodiments above, the ring member has an axial slot formed therein and wherein the tab member is designed to axially slide through the axial slot in the ring member.

Alternatively or additionally to any of the embodiments above, the rotation limiting member extends distally of the ring member.

Alternatively or additionally to any of the embodiments above, the rotation limiting member extends proximally of the ring member.

A hemostasis valve is disclosed. The hemostasis valve comprises: a main body including a threaded proximal end region having one or more threads; a first seal member disposed within the threaded proximal end region of the main body; a cartridge at least partially disposed within the threaded proximal end region of the main body, the cartridge including a second seal member; a nut threadably engaged with the threaded proximal end region of the main body; a plunger coupled to the threaded proximal end region of the main body, the plunger being designed to move relative to the threaded proximal end region of the main body; a ring member extending along the threaded proximal end region, the ring member being positioned distally of the one or more threads; a rotation limiting member positioned adjacent to the threaded proximal end region of the main body; and a tab member positioned adjacent to the threaded proximal end region of the main body, the tab member being designed to rotate relative to the threaded proximal end region of the main body until the tab member engages the rotation limiting member.

Alternatively or additionally to any of the embodiments above, the rotation limiting member is disposed along the threaded proximal end region of the main body, wherein the rotation limiting member extends distally of the ring member, and wherein outer surface of the tab member is disposed along the plunger.

Alternatively or additionally to any of the embodiments above, the rotation limiting member is disposed along an inner surface of the plunger and wherein the tab member is disposed along the threaded proximal end region of the main body at a position proximal of the ring member.

Alternatively or additionally to any of the embodiments above, the ring member has an axial slot formed therein and wherein the tab member is designed to axially slide through the axial slot in the ring member.

A hemostasis valve is disclosed. The hemostasis valve comprises: a main body including a threaded proximal end region having one or more threads; a first seal member disposed within the threaded proximal end region of the main body; a cartridge at least partially disposed within the threaded proximal end region of the main body, the cartridge including a second seal member; wherein the cartridge includes one or more projections, a helical groove region, and a stopping face; a nut threadably engaged with the threaded proximal end region of the main body; wherein the nut includes a guiding protrusion; and wherein the one or more projections, the stopping face, or both are designed to engage the guiding protrusion of the nut in order to limit rotation of the nut.

Alternatively or additionally to any of the embodiments above, further comprising a plunger coupled to the threaded proximal end region of the main body, the plunger being designed to move relative to the threaded proximal end region of the main body.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
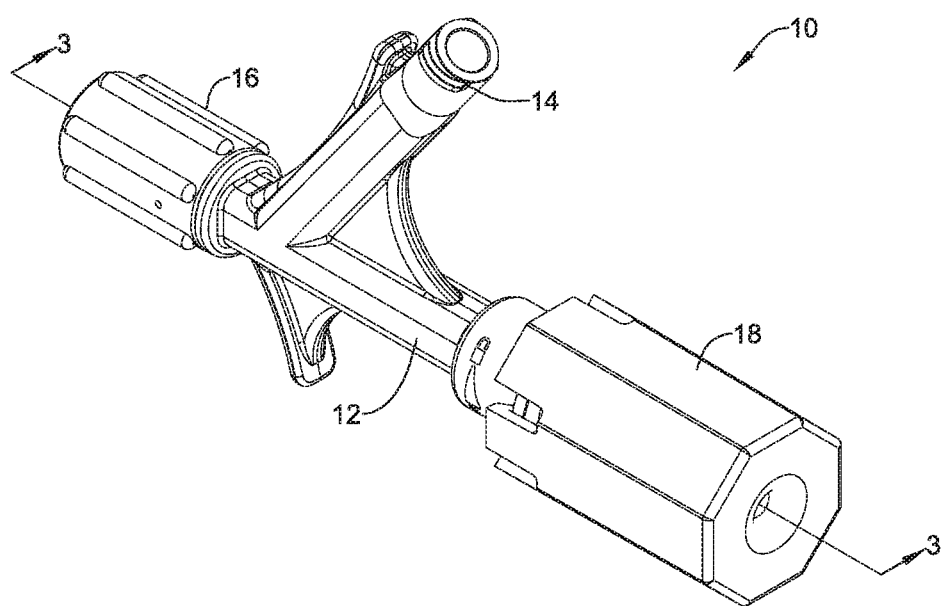
FIG. 1 is a perspective view of an example hemostasis valve.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, for example intravascular procedures, utilize medical devices within body lumens. For example, some intravascular procedures include the placement of a guidewire, guide catheter, interventional device, or the like in a blood vessel. Because fluid under pressure (e.g., blood) is present within the blood vessel, fluid could travel along or through the medical device and escape or leak from the patient. In some instances, it may be desirable to dispose a hemostasis valve or hemostasis valve assembly at the proximal end of a medical device to reduce or otherwise limit the leaking of fluids/blood from the proximal end of the device.

An example hemostasis valve 10 is shown in FIG. 1. The hemostasis valve 10 may include a main body 12. The main body 12 may include a side port 14. The side port 14 may be connected to another device such as an infusion device, an inflation device, or the like. An adapter 16 may be coupled to the distal end of the main body 12. The adapter 16 may be used to couple the hemostasis valve 10 to a device such as a catheter. A plunger 18 may be coupled to the proximal end of the main body 12. The plunger 18 may be used to activate or otherwise close a seal (e.g., as discussed herein) within the hemostasis valve 10. These and other features of the hemostasis valve 10 are discussed herein.

Figure 2:
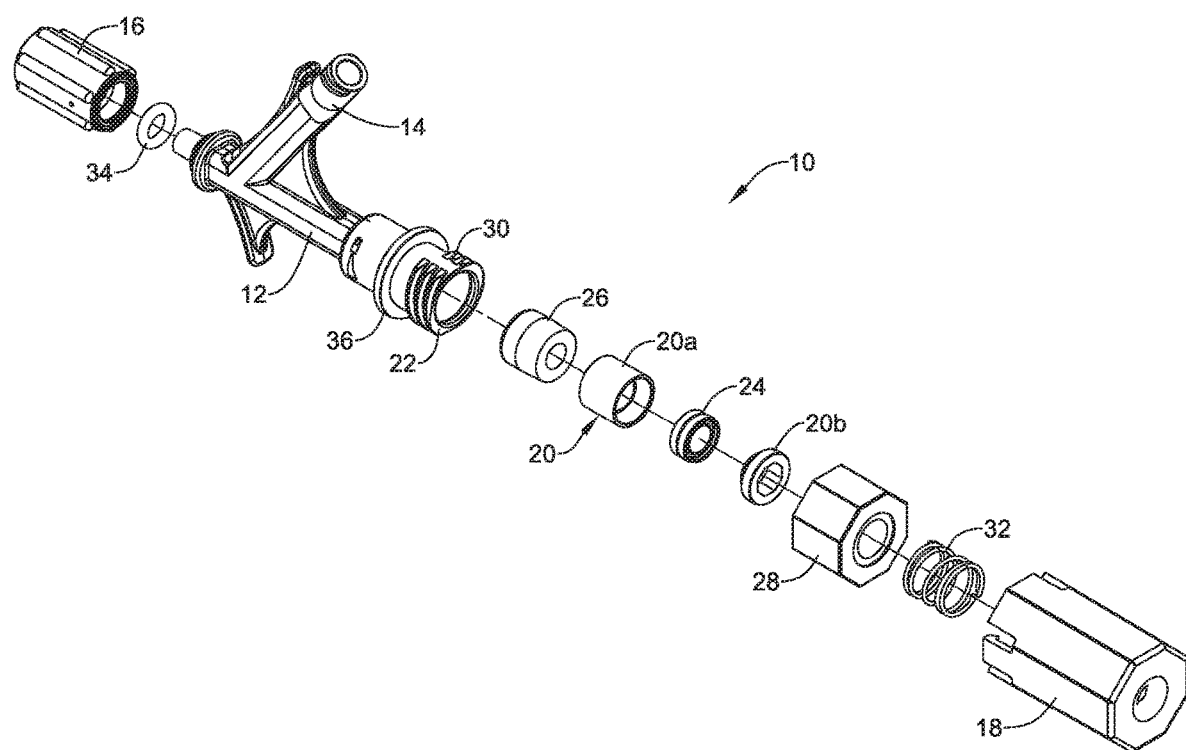
FIG. 2 is an exploded view of an example hemostasis valve.

FIG. 2 is an exploded view of the hemostasis valve 10. Here, the various components of the hemostasis valve 10 can be seen. For example, the hemostasis valve 10 may include a cartridge 20. The cartridge 20, which may include two pieces 20a, 20b that are coupled to one another (e.g., press fit, thermally bonded, adhesively bonded, etc.), may be arranged so that at least a portion thereof can be disposed within a proximal end region 22 of the main body 12. A first seal member 24 may be disposed within the cartridge 20. A second seal member 26 may be disposed within the proximal end region 22 of the main body 12. In at least some instances, the second seal member 26 may be disposed distally of the cartridge 20. The second seal member 26 may include a textured distal surface, grooves or wells formed therein, or the like. In addition or in the alternative, the second seal member 26 may include a proximal region with a reduced diameter. A nut 28 may be coupled to the proximal end region 22 of the main body 12, for example at one or more threads 30 formed along the proximal end region 22.

Other features of the hemostasis valve 10 that can be seen in FIG. 2 include a spring member 32 and an O-ring 34. The spring member 32 may be coupled to the plunger 18. In at least some instances, the spring member 32 may be designed to exert a proximally directed force on the plunger 18. The O-ring 34 may be positioned adjacent to the adapter 16. In addition, a ring member or "snap ring" 36 may be disposed along the proximal end region 22 of the main body 12.

Figure 3:
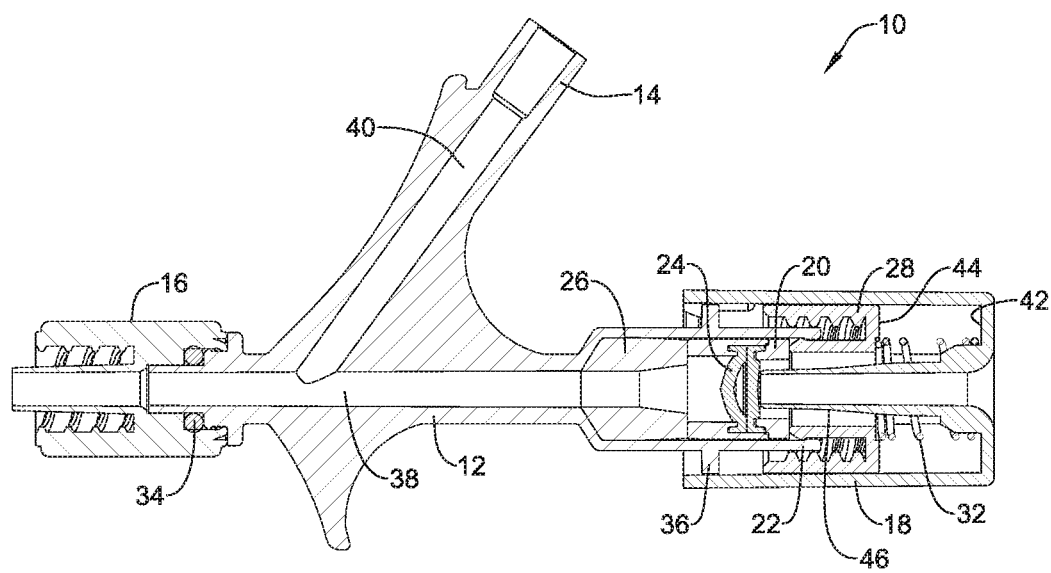
FIG. 3 is a cross-sectional view taken through line 3-3 in FIG. 1.

FIG. 3 is a cross-sectional view the hemostasis valve 10. Here some of the structural features of the hemostasis valve 10 can be seen. For example, the hemostasis valve 10 may include a central lumen 38. In general, the central lumen 38 is designed to be placed into fluid communication with one or more lumens of a device coupled to the adapter 16. A second or infusion lumen 40 may be defined adjacent to the side port 14. The second lumen 40 may be in fluid communication with the central lumen 38.

As indicated above, the hemostasis valve 10 is designed so that it may be coupled to another device. For example, the adapter 16, which may take the form of a Tuohy-Borst or other type of connector, may be engaged with the proximal end of the other device. When connected (and with the plunger 18 in the configuration shown in FIG. 3), the second seal member 26 may be in an open state or configuration. Conversely, the first seal member 24 may be in a closed or sealed configuration when the hemostasis valve 10 is connected to the other device (and with the plunger 18 in the configuration shown in FIG. 3).

Collectively, when the hemostasis valve 10 is connected to another device and in the configuration shown in FIG. 3, the hemostasis valve 10 is able to substantially hold a fluid-tight seal that substantially prevents the backflow and/or leakage of body fluids (e.g., blood). At some point during a medical intervention, it may be desirable to infuse additional fluids such as contrast media through the hemostasis valve 10. This may include attaching an infusion device to the side port 14. Because the first seal member 24 may be designed to substantially prevent the backflow and/or leakage of relatively-low pressure fluids, if the infusion device infuses fluids at a relatively high pressure, it is possible that the infusion fluid may be able to flow through the first seal member 24.

Figure 4:
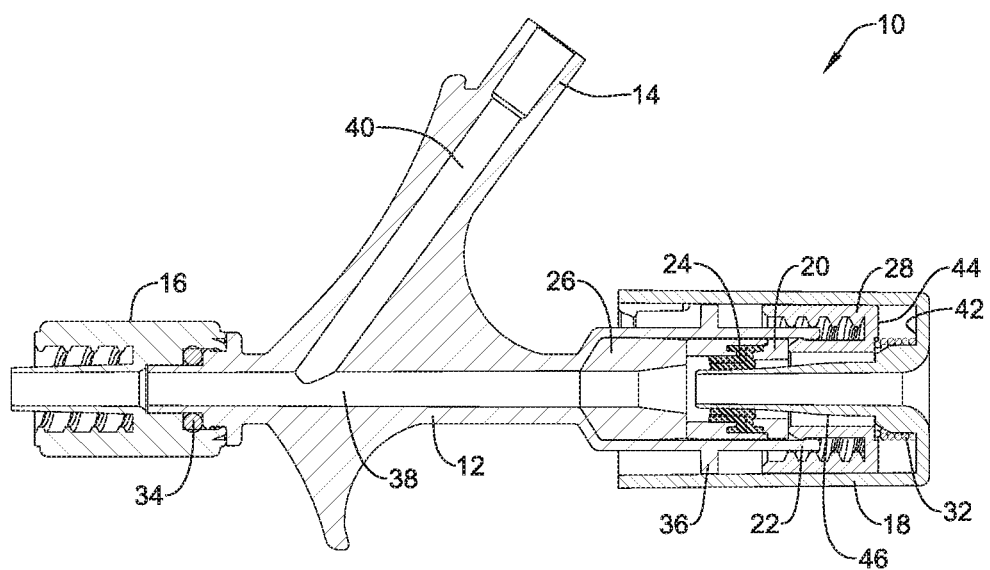
FIG. 4 is a cross-sectional view of an example hemostasis valve.
Figure 5A:
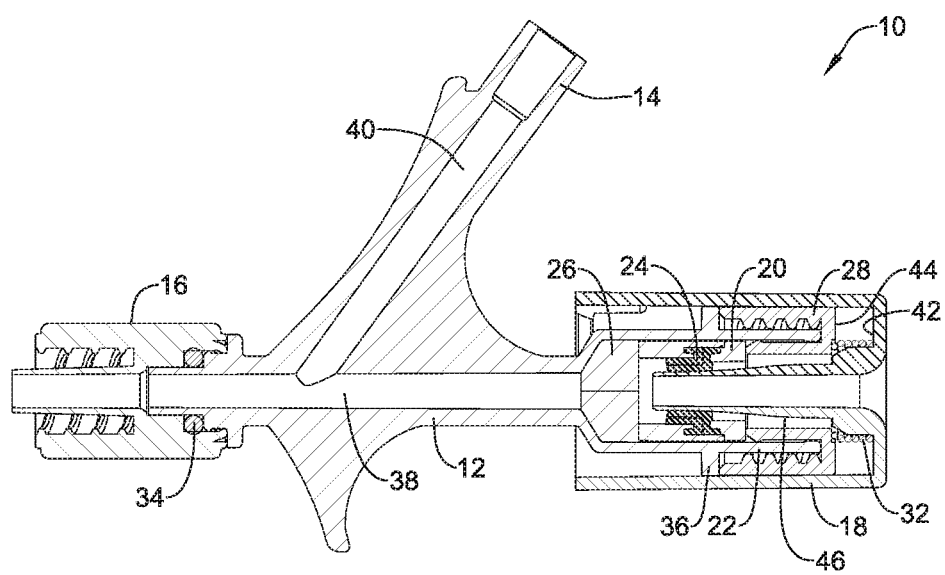
FIGS. 5A-5B is a cross-sectional view of an example hemostasis valve.
Figure 5B:
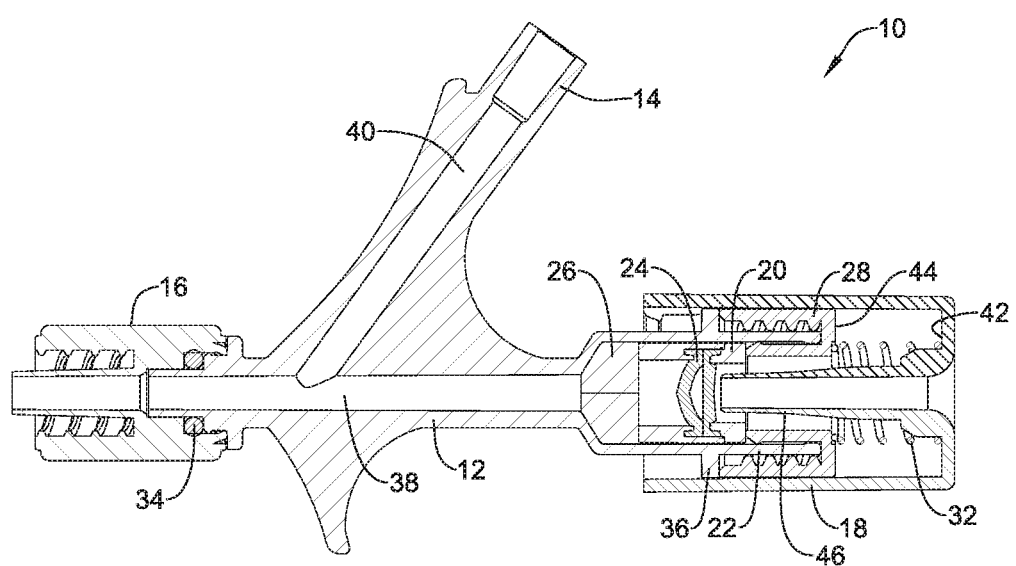

In order to prevent backflow of relatively high pressure fluids, the hemostasis valve 10 can be actuated to close or "seal" the second seal member 26. To do so, the plunger 18 may initially be urged distally until a distally-facing, proximal end surface or cap 42 of the plunger 18 is disposed adjacent to a proximal end region 44 of the nut 28 as shown in FIG. 4. When doing so, a tubular region 46 of the plunger 18 may extend through (and open) the first seal member 24. In addition, a portion of the plunger 18 may move distally beyond the ring member 36. With the cap 42 of the plunger 18 disposed adjacent to the nut 28, the plunger 18 can be rotated (e.g., in a clockwise direction) to close the second seal member 26 as shown in FIG. 5A. This rotation may cause the nut 28 to rotate and move distally. Because the distal end region of the nut 28 may be engaged with the cartridge 20, distal movement of the nut 28 urges the cartridge 20 distally within the proximal end region 22 of the main body 12 such that the cartridge 20 engages and deforms the second seal member 26, thereby shifting the second seal member 26 to the closed or sealed configuration. The plunger 18 may be released or otherwise allowed to move proximally, as shown in FIG. 5B, which may reclose the first seal member 24 (while the second seal member 26 remains closed).

For the purposes of this disclosure, "clockwise" rotation of the plunger 18 and/or nut 28 may be understood as rotation of the plunger 18 in a clockwise direction relative to the main body 12 when looking at the plunger 18 from its proximal end. Similarly, "counter-clockwise" rotation of the plunger 18 and/or nut 28 may be understood as rotation of the plunger 18 in a counter-clockwise direction relative to the main body 12 when looking at the plunger 18 from its proximal end. This convention for clockwise/counter-clockwise is used throughout this disclosure.

At some point during an intervention, it may be desirable to "re-open" the second seal member 26. In order to do so, the process described above may be reversed. For example, the plunger 18 may be rotated in the counter-clockwise direction, along with the nut 28, so that the nut 28 and the cartridge 20 move in the proximal direction, thereby relieving the forces applied to the second seal member 26. In some instances, it may be possible that the counter-clockwise rotation of the plunger 18 could continue (e.g., counter-clockwise rotation of the plunger 18 and/or the nut 28) to a point beyond what is needed to re-open the second seal member 26 and to a point where the nut 28 may be un-threaded from the threads 30 along the proximal end region 22. If this happens, it may not be practical to continue using the hemostasis valve 10 as it may not be practical to close the second seal member 26 again. Thus, it may be necessary to replace the hemostasis valve 10 in order to utilize the second seal member 26. It may be desirable to reduce the possibility of the nut 28 becoming un-threaded from the proximal end region 22 of the main body 12. Disclosed herein are hemostasis valves with structural features designed to reduce the possibility of the nut 28 becoming un-threaded from the proximal end region 22 of the main body 12.

Figure 6:
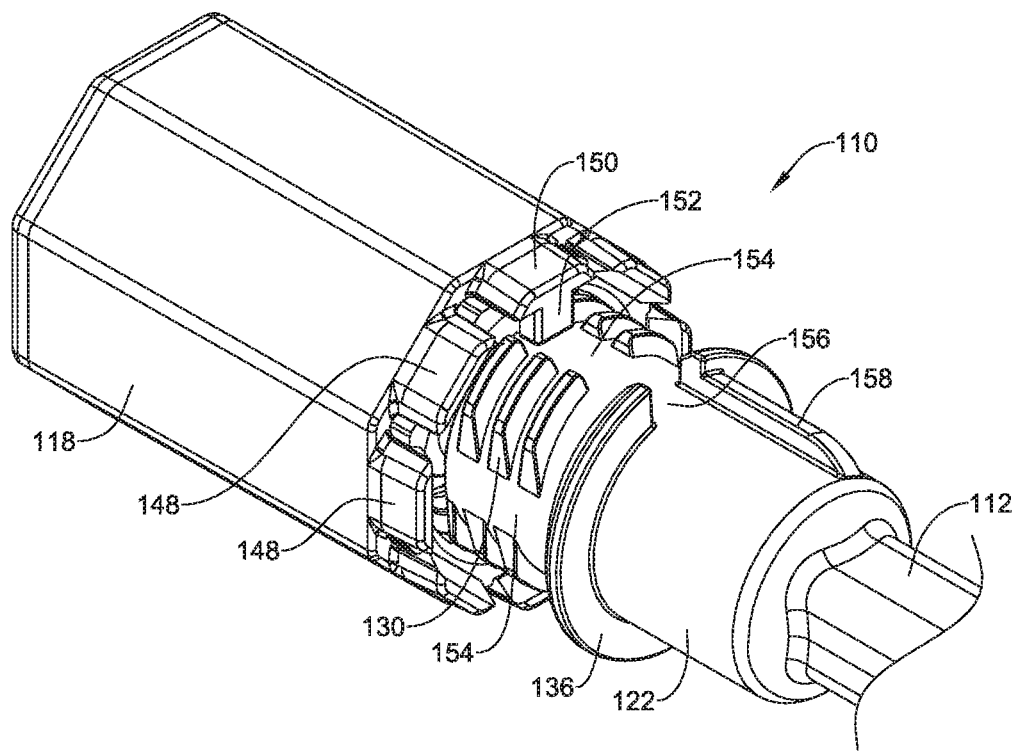
FIG. 6 is a perspective view of a portion of an example hemostasis valve.
Figure 7:
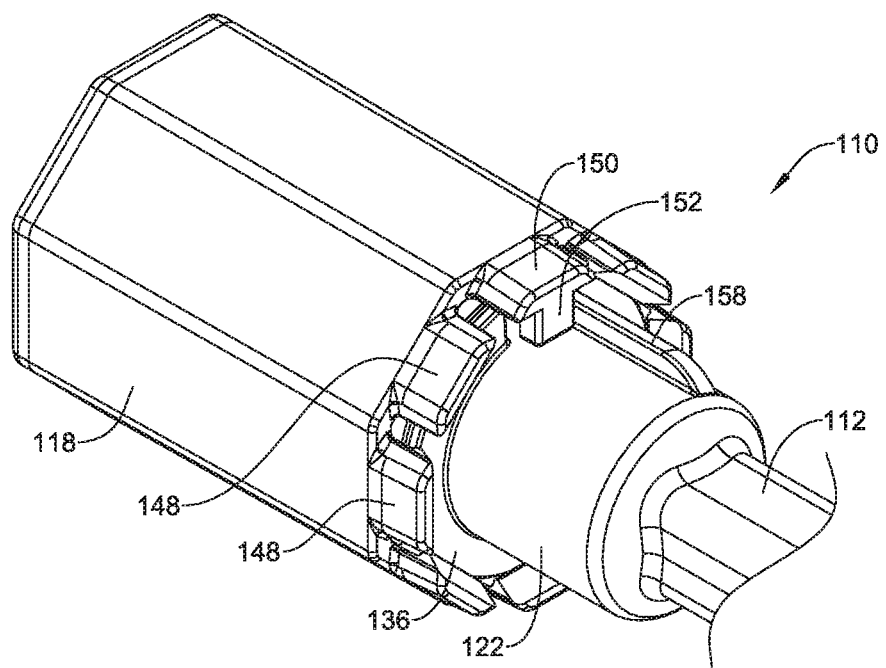
FIG. 7 is a perspective view of a portion of an example hemostasis valve.

FIG. 6 illustrates a portion of another example hemostasis valve 110 that may be similar in form and function to other hemostasis valves disclosed herein. While only a portion of the hemostasis valve 110 is shown, it can be appreciated that the reminder of the hemostasis valve 110 may include structures similar to or the same as those in the hemostasis valve 10 described above. The hemostasis valve 110 includes a main body 112 having a proximal end region 122. A plunger 118 is coupled to the proximal end region 122. The plunger 118 includes one or more snap members 148. In general, the snap members 148 may be designed to move distally beyond (e.g., "snap" past) a ring member 136 disposed along the proximal end region 122. At least one of the snap members 148, labeled with reference number 150 in FIG. 6, may include a tab member or locking tab 152. The locking tab 152 may be designed to translate through a slot or opening 154 in the threads 130 formed along the proximal end region 122 and through a slot or opening 156 in the ring member 136 when the plunger 118 is moved distally as shown in FIG. 7. When the locking tab 152 passes through the opening 156 (e.g., and when the locking tab 152 is positioned distally of the ring member 136), the plunger 118 can be rotated in the clockwise direction as shown in FIG. 7. This may cause a nut (not shown in FIGS. 6-7, but may be similar in form and function to the nut 28 as disclosed herein) to move distally and exert a force on a cartridge (not shown in FIGS. 6-7, but may be similar in form and function to the cartridge 20 as disclosed herein). This may cause a second seal member (not shown in FIGS. 6-7, but may be similar in form and function to the second seal member 26 as disclosed herein) to shift to a closed or sealed configuration.

When it is desired to re-open the second seal member, the plunger 118, while the locking tab 152 is still positioned distally of the ring member 136, can be rotated in the counter-clockwise direction. When doing so, the locking tab 152 may rotate about the proximal end region 122 and become engaged with a rotation limiting member or locking rib 158 formed along the proximal end region 122 of the main body 112. The engagement of the locking tab 152 with the locking rib 158 may limit the amount of or otherwise prevent further counter-clockwise rotation of the plunger 118 and/or the nut. Thus, further rotation of the nut including rotation that may lead to the nut becoming un-threaded from the threads 130 of the main body of the hemostasis valve 110 can be limited/prevented.

Figure 8:
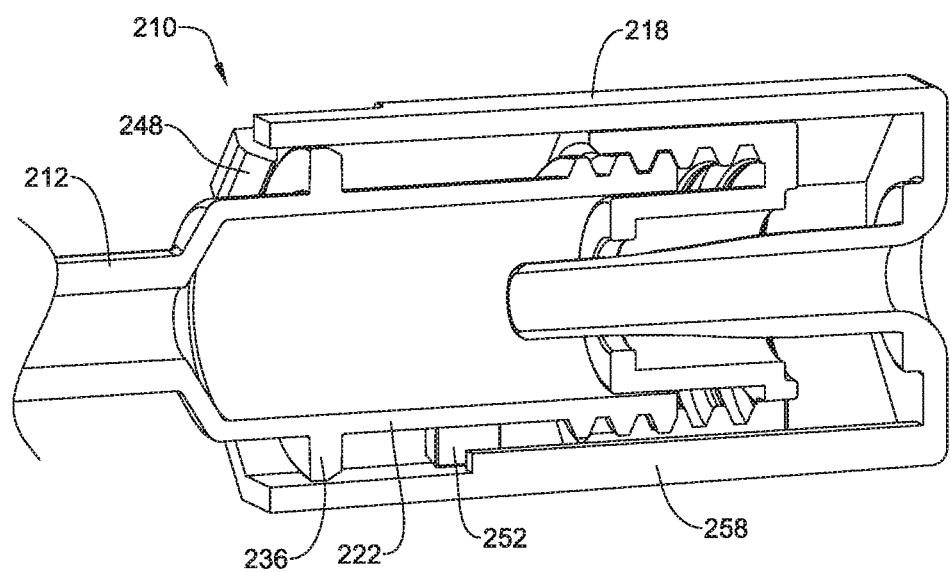
FIG. 8 is a perspective view of a portion of an example hemostasis valve.
Figure 9:
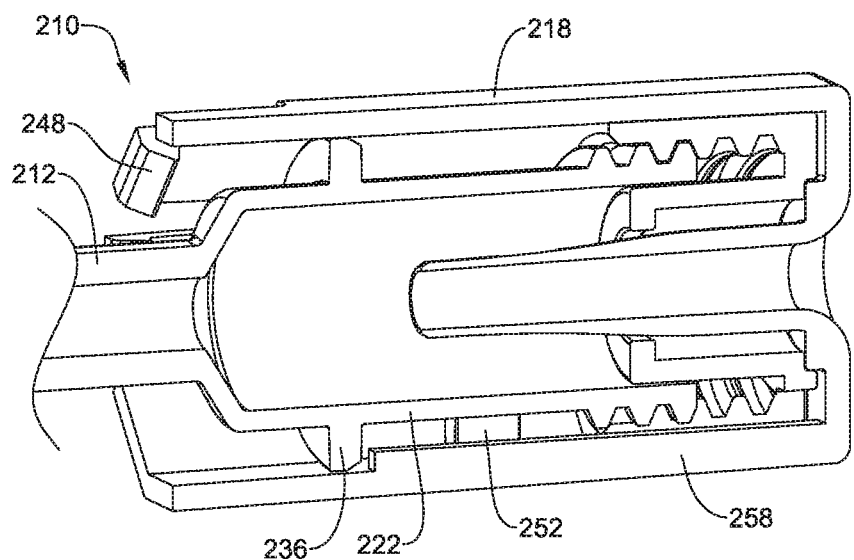
FIG. 9 is a perspective view of a portion of an example hemostasis valve.

FIGS. 8-9 illustrate a portion of another example hemostasis valve 210 that may be similar in form and function to other hemostasis valves disclosed herein. The hemostasis valve 210 includes a main body 212 having a proximal end region 222. A plunger 218 is coupled to the proximal end region 222. The plunger 218 includes one or more snap member 248. In this example, the rotation limiting features are located underneath the plunger 218 and/or proximal of the ring member 236. For example, a rotation limiting member or locking rib 252 may be formed along a surface of the proximal end region 222 of the main body 212. A tab member or locking tab 258 may be formed along the plunger 218. Thus, when the plunger 218 is moved distally (e.g., as shown in FIG. 9), the plunger 218 can be rotated in the clockwise direction (e.g., and the nut can be rotated to close the second seal member). When it is desired to re-open the second seal member, the plunger 218 can be rotated in the counter-clockwise direction until the locking tab 258 engages the locking rib 252.

Figure 10:
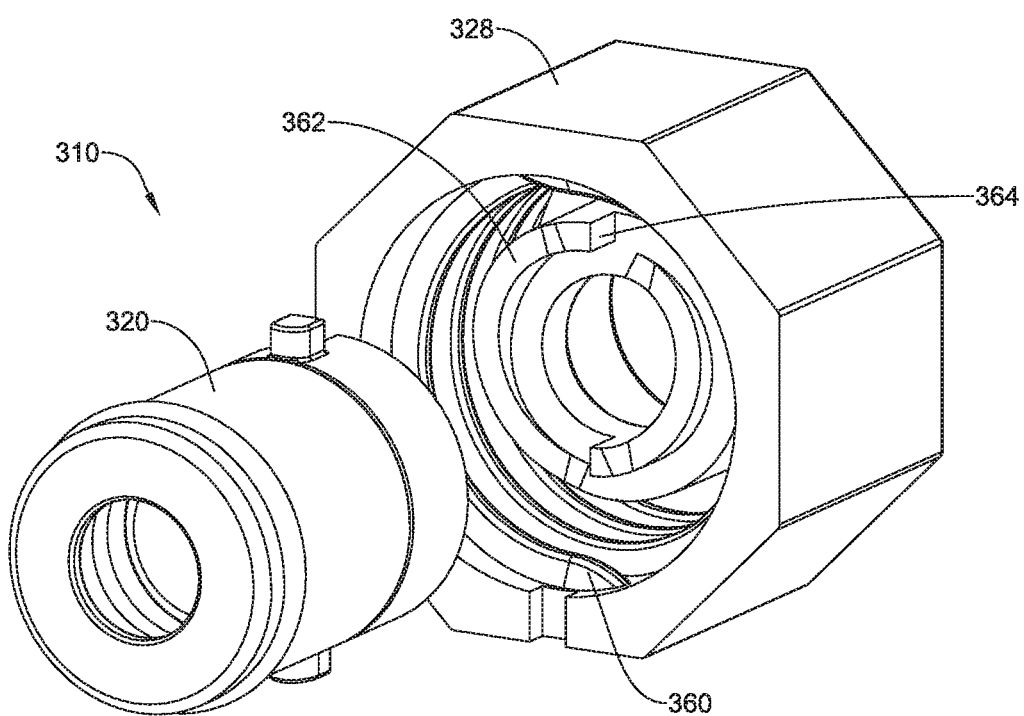
FIG. 10 is a perspective view of a portion of an example hemostasis valve.
Figure 11:
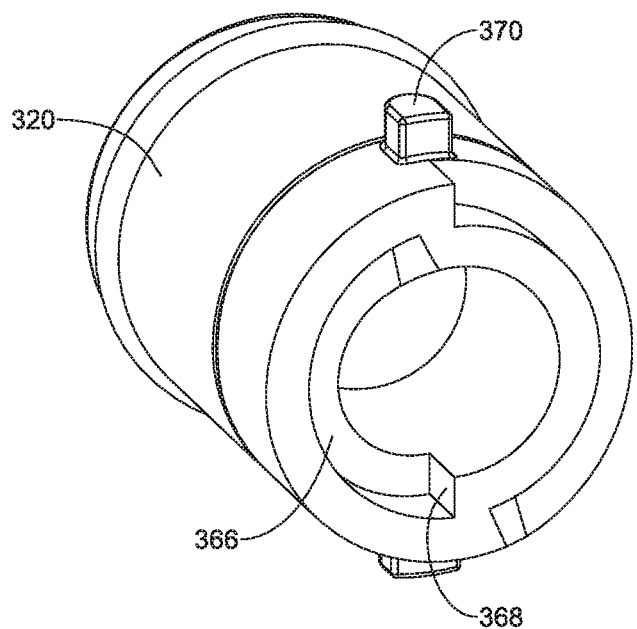
FIG. 11 is a perspective view of a portion of an example hemostasis valve.

FIGS. 10-11 illustrate a portion of another example hemostasis valve 310 that may be similar in form and function to other hemostasis valve disclosed herein. In this example, only a cartridge 320 (similar in form and function to the cartridge 20 disclosed herein) and a nut 328 (similar in form and function to the nut 28 disclosed herein) of the hemostasis valve 310 are shown. The nut 328 may include internal threads 360 that are designed to threadably engage threads formed along a proximal end region of a main body of the hemostasis valve 310 (e.g., threads that are the same as or similar to the threads 30 disclosed herein along the proximal end region 22 of the main body 12 as disclosed herein). In addition, the nut 328 may include a tab member or guiding protrusion 362 having a face 364.

The cartridge 320 may include a helical groove 366 and a rotation limiting member or stopping face 368. When fitted together, the guiding protrusion 362 of the nut 328 is designed to fit within the groove 366. This arrangement allows the nut 328 to be rotated in a clockwise direction. However, when the nut 328 is rotated in the counter-clockwise direction, the face 364 along the guiding protrusion 362 will eventually engage the stopping face 368 formed along the groove 366. This will help to limit further counter-clockwise rotation of the nut 328. Thus, when it is desired to re-open the second seal member, the plunger (e.g., not shown in FIGS. 10-11, but may be similar to other plungers disclosed herein) and/or the nut 328 can be rotated in the counter-clockwise direction until the face 364 engages the stopping face 368. In some instances, the structural arrangement of the guiding protrusion 362 and the groove 366 may also limit clockwise rotation of the nut 328 relative to the cartridge 320. This may help prevent the second seal member from being deformed to an extent beyond what is needed to effectively close the second seal member and/or reduce possible damage of the second seal member.

In some instances, the cartridge 320 may include one or more projections 370. The projections 370 may help reduce rotation of the cartridge 320 when the plunger and/or nut 328 are rotated. For example, in some instances, the projections 370 may fit within slots or recesses (not shown) formed in the proximal end region of the main body of the hemostasis valve. Some additional details regarding the projections 370 and other structural feature for use therewith are disclosed in U.S. Patent Application No. 62/470,634, filed on even date herewith and incorporated herein by reference.

The materials that can be used for the various components of the hemostasis valve 10 (and/or other hemostasis valves disclosed herein) and the various components thereof disclosed herein may include those commonly associated with medical devices. For simplicity purposes, the following discussion makes reference to the main body 12 and other components of the hemostasis valve 10. However, this is not intended to limit the devices and methods described herein, as the discussion may be applied to other hemostasis valves and/or components thereof disclosed herein.

The main body 12 and/or other components of the hemostasis valve 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A hemostasis valve, comprising: a main body having a distal end region and a proximal end region; a cartridge at least partially disposed within the proximal end region of the main body, the cartridge including a first seal member; a second seal member disposed within the proximal end region of the main body; a plunger coupled to the proximal end region of the main body, the plunger configured to slide axially relative to the main body along a longitudinal axis thereof; a rotation limiting member positioned adjacent to the proximal end region of the main body; and a tab member positioned adjacent to the proximal end region of the main body, the tab member being designed to rotate relative to the proximal end region of the main body until the tab member engages the rotation limiting member.

2. The hemostasis valve of claim 1, wherein the rotation limiting member is disposed along an outer surface of the main body.

3. The hemostasis valve of claim 2, wherein the tab member is disposed along the plunger.

4. The hemostasis valve of claim 1, wherein the rotation limiting member is disposed along an inner surface of the plunger.

5. The hemostasis valve of claim 4, wherein the tab member is disposed along the proximal end region of the main body.

6. The hemostasis valve of claim 1, wherein the proximal end region of the main body includes one or more threads.

7. The hemostasis valve of claim 6, further comprising a nut threadably engaged with the one or more threads.

8. The hemostasis valve of claim 7, wherein the rotation limiting member comprises a stopping face formed on the cartridge, wherein the tab member comprises a guiding protrusion formed along the nut.

9. The hemostasis valve of claim 7, wherein an axial slot is formed in the one or more threads.

10. The hemostasis valve of claim 9, wherein the tab member is designed to axially slide along the axial slot in the one or more threads.

11. The hemostasis valve of claim 1, wherein a ring member is disposed about the proximal end region of the main body.

12. The hemostasis valve of claim 11, wherein the ring member has an axial slot formed therein and wherein the tab member is designed to axially slide through the axial slot in the ring member.

13. The hemostasis valve of claim 11, wherein the rotation limiting member extends distally of the ring member.

14. The hemostasis valve of claim 11, wherein the rotation limiting member extends proximally of the ring member.

15. A hemostasis valve, comprising: a main body including a threaded proximal end region having one or more threads; a cartridge at least partially disposed within the threaded proximal end region of the main body, the cartridge including a first seal member; a second seal member disposed within the threaded proximal end region of the main body; a nut threadably engaged with the threaded proximal end region of the main body; a plunger coupled to the threaded proximal end region of the main body, the plunger being designed to move relative to the threaded proximal end region of the main body; a ring member extending along the threaded proximal end region, the ring member being positioned distally of the one or more threads; a rotation limiting member positioned adjacent to the threaded proximal end region of the main body; and a tab member positioned adjacent to the threaded proximal end region of the main body, the tab member positioned adjacent to the threaded proximal end region of the main body, the tab member being designed to rotate relative to the threaded proximal end region of the main body until the tab member engages the rotation limiting member.

16. The hemostasis valve of claim 15, wherein the rotation limiting member is disposed along an inner surface of the plunger and wherein the tab member is disposed along the threaded proximal end region of the main body at a position proximal of the ring member.

17. The hemostasis valve of claim 15, wherein the ring member has an axial slot formed therein and wherein the tab member is designed to axially slide through the axial slot in the ring member.

18. The hemostasis valve of claim 15, wherein the rotation limiting member is disposed along the threaded proximal end region of the main body, wherein the rotation limiting member extends distally of the ring member, and wherein outer surface of the tab member is disposed along the plunger.

19. A hemostasis valve, comprising: a main body including a threaded proximal end region having one or more threads; a cartridge at least partially disposed within the treaded proximal end region of the main body, the cartridge including a first seal member; wherein the cartridge includes one or more projections, a helical groove region, and a stopping face; a second seal member disposed within the threaded proximal end region of the main body; a nut threadably engaged the threaded proximal end region of the main body; wherein the nut includes a guiding protrusion; and wherein the one or more projections, the stopping face, or both are designed to engage the guiding protrusion of the nut in order to limit rotation of the nut.

20. The hemostasis valve of claim 19, further comprising a plunger coupled to the threaded proximal end region of the main body, the plunger being designed to move relative to the threaded proximal end region of the main body.

* * * * *